United States Patent
Peterson et al.

(10) Patent No.: US 7,867,240 B2
(45) Date of Patent: * Jan. 11, 2011

(54) DEVICES AND METHODS FOR STORING, LOADING, AND DELIVERING AN INTRAOCULAR LENS

(75) Inventors: Rod T Peterson, Tustin Ranch, CA (US); Robert D Ott, Irvine, CA (US); Mark S Cole, Trabuco Canyon, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 63 days.

This patent is subject to a terminal disclaimer.

(21) Appl. No.: 12/265,649

(22) Filed: Nov. 5, 2008

(65) Prior Publication Data

US 2009/0062811 A1    Mar. 5, 2009

Related U.S. Application Data

(63) Continuation of application No. 11/071,549, filed on Mar. 2, 2005, now Pat. No. 7,458,976.

(51) Int. Cl.
*A61F 9/00*    (2006.01)
(52) U.S. Cl. ..................................... 606/107; 623/6.12
(58) Field of Classification Search ................ 606/107, 606/4, 5, 6, 108; 623/6.11–6.12; 604/57, 604/59, 64
See application file for complete search history.

(56) References Cited

U.S. PATENT DOCUMENTS

| | | | |
|---|---|---|---|
| 5,123,905 A | 6/1992 | Kelman | |
| 5,190,552 A | 3/1993 | Kelman | |
| 5,902,307 A | 5/1999 | Feingold et al. | |
| 5,947,974 A | 9/1999 | Brady et al. | |
| 6,056,757 A | 5/2000 | Feingold et al. | |
| 6,447,520 B1 | 9/2002 | Ott et al. | |
| 6,540,754 B2 | 4/2003 | Brady | |
| 6,712,848 B1 | 3/2004 | Wolf et al. | |
| 6,733,507 B2 | 5/2004 | McNicholas et al. | |

FOREIGN PATENT DOCUMENTS

| | | |
|---|---|---|
| EP | 1262154 A1 | 12/2002 |
| FR | 2820633 | 2/2001 |
| FR | 2820633 | 8/2002 |

*Primary Examiner*—Gary Jackson
*Assistant Examiner*—Gregory Anderson

(57) ABSTRACT

A cartridge for delivering an intraocular lens into the eye of a subject that comprises a body disposed along a longitudinal axis having a distal end and a proximal end, and a tapered lumen disposed along the longitudinal axis having an aperture at the distal end of the body. The aperture and at least a portion of the tapered lumen each consist of an upper portion and a lower portion. The upper portions of the aperture and lumen each have a first width and a cross-section that is generally arcuate. The lower portions of the aperture and lumen each have a cross-section that is generally horizontally disposed and have a second width that is greater than the first width of the aperture and lumen. The cartridge may be loaded with an intraocular lens using a packaging system. The intraocular lens may be placed into the eye of a subject using a corresponding inserter having a pushrod with a saddle disposed at the tip thereof. The intraocular lens is preferably draped over the saddle during insertion.

5 Claims, 15 Drawing Sheets

DEVICES AND METHODS FOR STORING, LOADING, AND DELIVERING AN INTRAOCULAR LENS

This application is a continuation application and claims priority to U.S. application Ser. No. 11/071,549 filed on Mar. 2, 2005, the entire contents of which are hereby incorporated by reference in its entirety for all purposes as if fully set forth herein.

BACKGROUND OF THE INVENTION

1. Field of the Invention

The invention relates generally to systems and methods for handling an intraocular lens and more specifically to systems and methods for storing an intraocular lens, loading an intraocular lens into a cartridge, and for delivering the intraocular lens from the cartridge into the eye of a subject.

2. Description of the Related Art

It is estimated that at least about 42% of Americans between the ages of 52 and 64 and 73% of Americans between the ages of 65 to 74 get cataracts. A cataract is a clouding of the eye's lens that impairs a person's vision and, if left untreated, causes blindness. As a result, each year approximately 1.4 million people in the United States alone undergo cataract surgery, whereby the clouded lens is removed and replaced with an intraocular lens (IOL) implant.

A typical IOL includes an optic or lens body for focusing light toward the retina of the eye. In addition, the IOL also includes one or more fixation members or haptics for securing the IOL in the desired position within the chamber of the eye. The IOL is implanted directly into the eye through a small incision formed in the ocular tissue of the eye. To fit through this small incision, modern IOLs are designed to be deformed, e.g., rolled, folded or the like, to a relatively small profile and then allowed to return to their original shape within the eye.

A useful technique for inserting an IOL into the eye includes use of an IOL injector or cartridge. Conventional IOL cartridges include a load chamber connected to an injection tube. Typically, the load chamber further includes an openable first lumen for receiving the IOL. Closure of this first lumen folds the IOL and maintains the IOL in a folded state. The injection tube includes a small diameter distal tip that is insertable into the incision within the eye. The IOL may be delivered from the load chamber through the injection tube and into the eye.

In general, the IOL is provided to the surgeon in packaging, such as a vial, plastic blister package, or other container for maintaining the IOL in a sterile condition. The IOL is removed from the packaging and placed on the open load chamber prior to insertion into the patient's eye. The packaging protects the IOL during handling and transportation to the surgical site and maintains the sterility of the IOL prior to use.

The technique of removing the IOL from the packaging and transferring it to the load chamber is usually accomplished with a pair of forceps or similar device. Any covering of the packaging is removed so that the IOL is exposed in its container. Insertion forceps are used to remove the IOL from the packaging and subsequently fold the IOL to a reduced size for insertion into the eye. Alternatively, the forceps are used to physically remove the IOL from the packaging and place it on the load chamber of the cartridge. Whether folding the IOL or simply loading it into the cartridge, this step requires particular manual dexterity and surgical skills.

In this regard, a variety of problems may arise when removing the IOL from its packaging, manually folding the IOL and/or placing the IOL into an insertion device or cartridge. For example, if proper care is not exercised during manipulation of the IOL, the IOL can be dropped and/or damaged. In addition, the IOL can be damaged if improperly folded or loaded into the cartridge and insertion device. Further, IOL sterility may be compromised if the IOL is not handled properly during the unpacking and loading procedures, thereby requiring the IOL to be discarded.

Other problems may be encountered during delivery of the IOL from the cartridge and into the eye of the subject. For instance, because the IOL is rolled inside the load chamber and/or injection tube, the orientation of the optic and haptic portions may be difficult to control. In addition, problems may be encountered regarding engagement of the tip of the push-rod with the IOL, resulting in damage of optic, haptics, or both.

In view of the above, there is a need for systems and methods that simplify and enhance the storage, transfer, and delivery of IOLs.

SUMMARY OF THE INVENTION

The present invention contemplates an intraocular lens (IOL) storage and insertion system that includes a lens loading function, and satisfies related doctor and/or support staff needs.

The present invention further contemplates a device to store and transfer an intraocular lens. The device comprises an intraocular lens and a tray having an aperture, wherein the intraocular lens is housed within a portion of the aperture and wherein another portion of the aperture is configured to house a lens cartridge. The device may also include a loading mechanism in communication with the tray, wherein the loading mechanism causes controlled movement of the intraocular lens within the device.

The present invention also contemplates a method of storing an intraocular lens and transferring said intraocular lens to a lens cartridge for use in a delivery device. The method comprises providing a packaging device housing an intraocular lens and a lens cartridge within a tray of the packaging device, wherein the packaging device further comprises a loading tool in communication with the tray. The method also includes distally advancing the loading tool to transfer and secure the intraocular lens within the lens cartridge. Finally, the method includes proximally retracting the loading tool to release the intraocular lens and the lens cartridge, and removing the lens cartridge from the packaging device, wherein the lens cartridge now contains the intraocular lens.

One aspect of the present invention involves a cartridge for delivering an intraocular lens into the eye of a subject that comprises a body disposed along a longitudinal axis having a distal end and a proximal end. The cartridge further comprises a tapered lumen disposed along the longitudinal axis having an aperture at the distal end of the body. The aperture and at least a portion of the tapered lumen each consist of an upper portion and a lower portion. The upper portions of the aperture and lumen each have a first width and a cross-section that is generally arcuate. The lower portions of the aperture and lumen each have a cross-section that is generally horizontally disposed and have a second width that is greater than the first width of the aperture and lumen.

Another aspect of the present invention involves an insertion system for delivering an intraocular lens into the eye of a subject comprising a cartridge and a handpiece. The cartridge has a longitudinal axis, a load chamber for receiving an intraocular lens. The cartridge also contains a tapered lumen disposed along the longitudinal axis that has an aperture at a distal end thereof. The cartridge further has a bottom surface with an opening disposed along the longitudinal axis. The handpiece contains a pushrod with a tip having a saddle. The opening on the bottom surface of the cartridge is disposed to permit passage of at least a portion of the tip of the pushrod when cartridge is placed onto the handpiece from above the handpiece.

In yet another aspect of the present invention, a method of inserting an intraocular lens comprises providing a cartridge having a longitudinal axis, a load chamber, a tapered lumen, and a bottom surface. The load chamber is configured for receiving an intraocular lens having a haptic and an optic body. The tapered lumen is disposed along the longitudinal axis and has an aperture at a distal end thereof. The bottom surface has an opening disposed along the longitudinal axis. The method also comprises providing a handpiece having a pushrod with a tip having a saddle. The method further comprises disposing the cartridge above the handpiece and attaching the cartridge onto the handpiece from above the handpiece. While attaching the cartridge, the method also comprises disposing the tip such that the opening permits passage of at least a portion of the tip.

DESCRIPTION OF THE DRAWINGS

Embodiments of the present invention may be better understood from the following detailed description when read in conjunction with the accompanying drawings. Such embodiments, which are for illustrative purposes only, depict the novel and non-obvious aspects of the invention. The drawings include the following 25 figures, wherein like reference numerals in the written description designate identical or corresponding parts throughout the several views and embodiments of the invention illustrated in the figures.

Other features and advantages of the present invention will be seen as the following description of particular embodiments progresses in conjunction with the drawings, in which.

DETAILED DESCRIPTION

Figure 1:
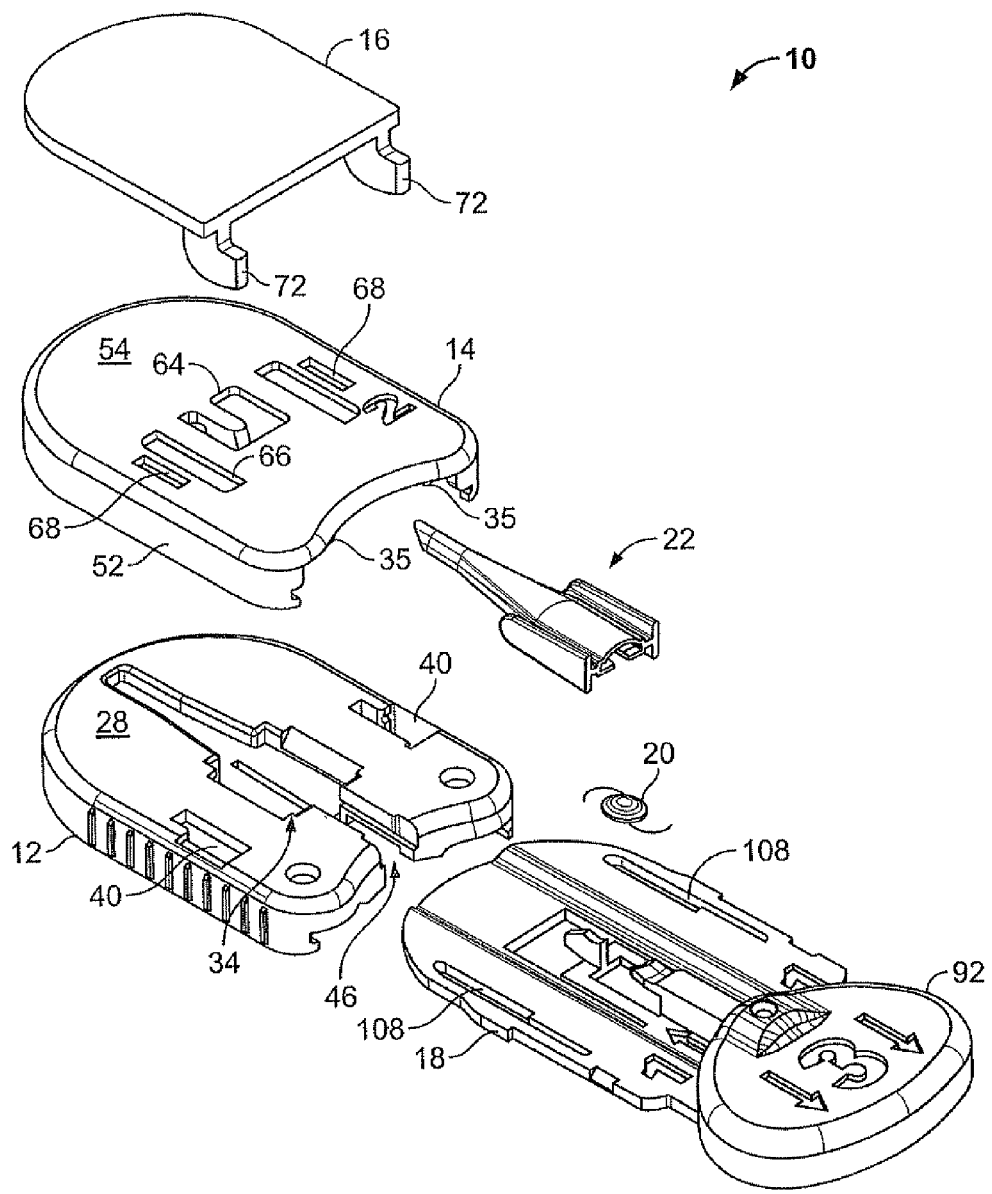
FIG. 1 is an exploded perspective view of an embodiment of a lens packaging system in accordance with the present invention.
Figure 2:
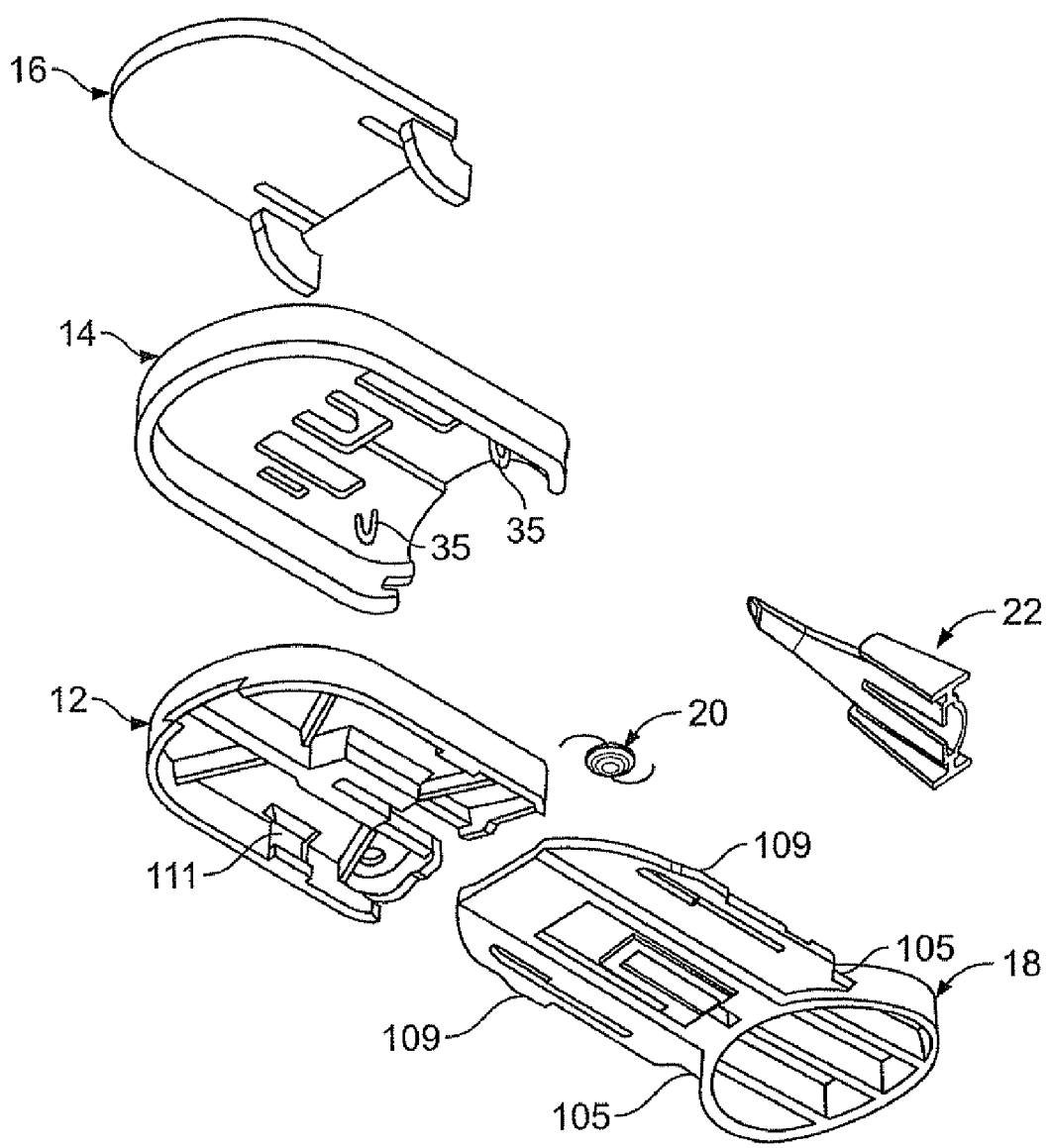
FIG. 2 is another exploded perspective view of the underside of an embodiment of a lens packaging system in accordance with the present invention.

Referring to FIGS. 1 and 2, a lens packaging system/lens loading system 10 in accordance with embodiments of the present invention includes a tray 12, a lid 14, a cover 16 and a loading tool 18. The tray 12 is configured to hold and store a foldable IOL 20 and a cartridge 22. In this regard, the IOL 20 and cartridge 22 are held within the tray 12 via the lid 14, cover 16 and loading tool 18. In addition to securing the IOL 20 and cartridge 22, the tray 12 also includes a lock (not shown) to secure the loading tool 18 during shipment and storage of the packaging system 10 and, thereby, prevent accidental activation of the loading tool 18.

In general, the packaging system 10 may be fabricated as a disposable, single-use component or a reusable, multi-use component. As such, a variety of materials may be used to fabricate the tray 12, lid 14, cover 16 and loading tool 18 of the packaging system 10. These materials include, but are not limited to, plastics, metals (such as stainless steel, aluminum or titanium), ceramics and the like, including combinations thereof. By way of illustrative example, with no limitation being intended or implied, the tray 12 is fabricated from polypropylene, and the lid 14 and loading tool 18 are fabricated from polycarbonate.

Figure 3:
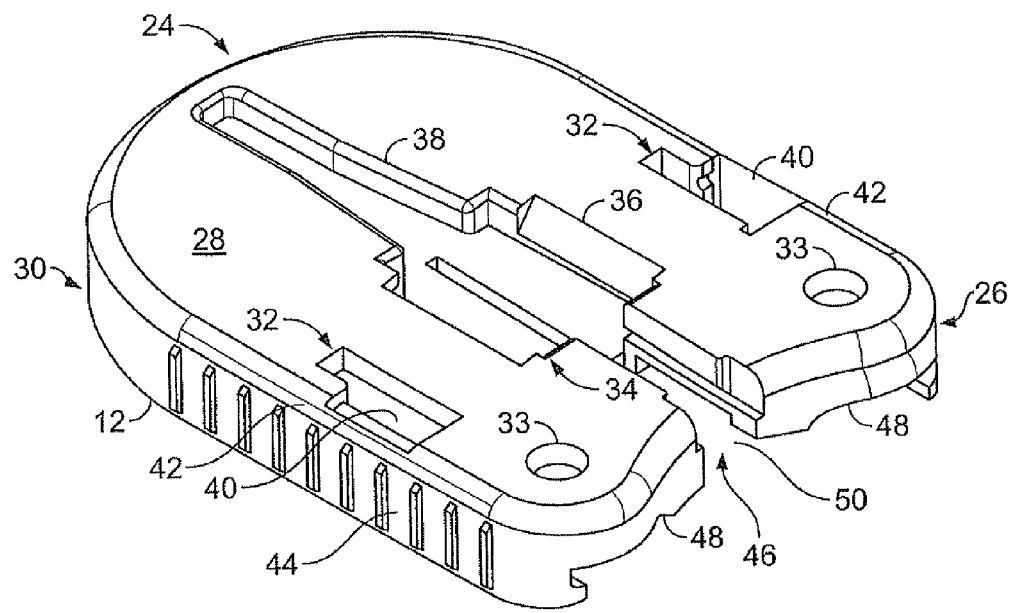
FIG. 3 is a perspective view of an embodiment of a tray of a lens packaging system in accordance with the present invention.

Referring to FIGS. 1, 2 and 3, in one embodiment of the packaging system 10, the tray 12 includes a distal end 24, a proximal end 26, a half-oval shaped top surface 28 and a sidewall 30. The distal end 24 of the tray 12 is rounded or curved to conform to the curved portion of the half-oval shaped top surface 28. The proximal end 26 of the tray 12 is also slightly curved or rounded and arches in the same direction as the distal end 24 of the tray 12. In general, the proximal end 26 of the tray 12 is configured to accommodate the loading tool 18 of the packaging system 10, as described in further detail below. Alternatively, in other embodiments (not shown), the distal and proximal ends 24, 26 of the tray 12 are arched in opposite directions. Furthermore, in certain embodiments, the distal and proximal ends 24, 26 of the tray 12 are angled to form a portion of a square, rectangle, triangle, quadrilateral, regular and/or irregular-shaped form.

As further illustrated in FIG. 3, the top surface 28 of the tray 12 is generally planar or flat and includes one or more indentations and/or apertures 32, 33, 34 formed therein. The apertures 32 are disposed to either side of the top surface 28 and guide elements or posts, for aligning the lid 14 and/or loading tool 18 of the packaging system 10. The proximal-most apertures 33 are formed as two round holes in the top surface 28 of the tray. These apertures or holes 33 are configured to accommodate the alignment pins of the lid 14, as explained in further detail below.

The center aperture 34 is configured to accommodate a lens 20 and lens cartridge 22, or similar lens holding and/or folding device. In the embodiment of the packaging system 10 illustrated in FIG. 3, the center aperture 34 is approximately cross-shaped and includes a wide transverse slot 36 that intersects a narrow, elongate longitudinal slot 38 extending approximately from the proximal end 26 to the distal end 24 of the tray. The center aperture 34 further includes various chamfers and ridges within each slot 36, 38, which provide additional support and stability for the lens cartridge 22. As such, during storage and/or prior to use of the system 10, it is the narrow, distal section of the longitudinal slot 38 together with the wide transverse slot 36 that house the cartridge 22, whereas the narrow, proximal section of the central aperture's longitudinal slot 38 that houses the IOL 20.

Adjacent the center aperture 34 are two additional longitudinal side-slots 40. Each side-slot 40 is positioned on either side and in alignment with the wide transverse slot 36 of the center aperture 34. In general, the side-slots 40 are approximately L-shaped and extend along the longitudinal axis near the side edges 42 of the tray 12. The side-slots 40 are designed to accommodate the guideposts of the cover 16, as described in further detail below.

Integral with the top surface 28 of the tray 12 is a sidewall 44. The sidewall 44 extends along the perimeter of the top surface 28 and forms a hollow cavity beneath the top surface 28 of the tray 12. As illustrated in FIG. 3, an opening 46 extends along a portion of the sidewall 44 located near the tray's proximal end 26. In particular, the opening 46 includes a first portion 48 and a second portion 50, wherein the first portion 48 of the opening 46 extends along a transverse, proximal section of the tray's sidewall 44. The second portion 50 of the opening 46 forms a longitudinal slot that is continuous with the first portion 48 and extends in a distal direction along the top surface 28 of the tray 12. In particular, the second portion 50 of the opening 46 merges with the central aperture 34 of the top surface 28. In general, the opening 46 is configured to accommodate the loading tool 18 of the packaging system 10, as described in further detail below.

Figure 4:
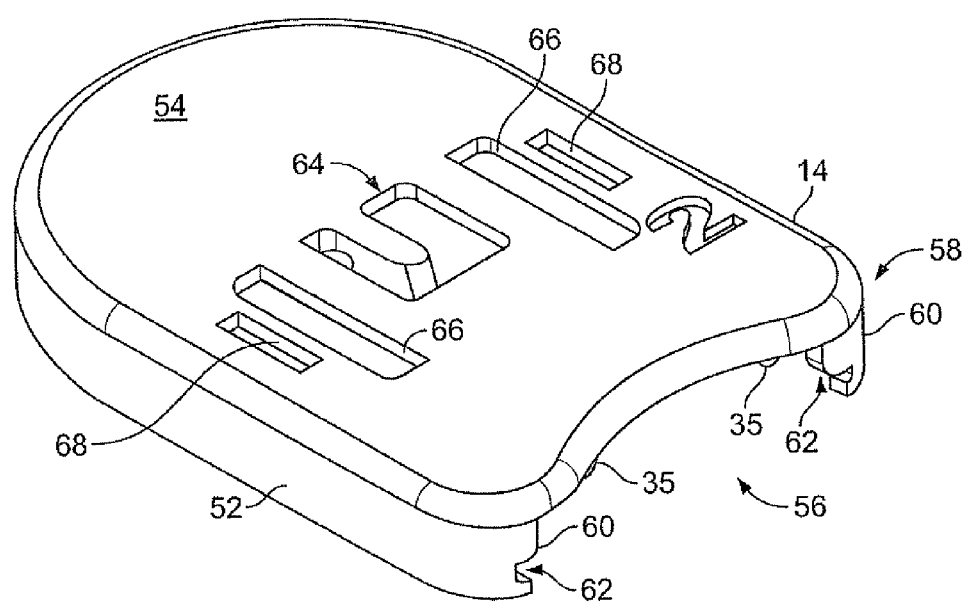
FIG. 4 is a perspective view of an embodiment of a lid of a lens packaging system in accordance with the present invention.

Referring to FIGS. 1, 2 and 4, the shape of the lid 14 is nearly identical to the shape of the tray 12. However, as seen in FIG. 4, the sidewall 52 of the lid 14 does not extend completely around the perimeter of the lid's top surface 54 but, rather, includes a generally rectangular-shaped gap or aperture 56 near the proximal end 58 of the lid 14. In addition, each vertical edge 60 of the sidewall 52 that frames the gap or aperture 56 further includes at least one notch 62, which is continuous with the aperture 56 near the proximal end 58 of the lid 14. As explained in further detail below, the lid's aperture and notches 56, 62, which are in direct alignment with the longitudinal slot 46 of the tray 12, are generally configured to accommodate the loading tool 18 when fully advanced during transfer of the IOL 20 into the cartridge 22.

In addition to differences in the sidewalls 44, 52, there are also slight differences in the apertures/indentations formed in the top surfaces 28, 54 of the tray 12 and lid 14. In particular, as shown in FIG. 4, the proximal end of the lid's top surface 54 does not include apertures or indentations, as does the tray 12. However, as seen in FIG. 2, the underside of the lid 14, near its proximal end, may include one or more alignment pins 35. As explained above, these alignment pins 35 are configured to seat within the proximal-most apertures 33 of the tray 12 and, thereby, align and secure the lid 14 onto the tray 12 of the device 10.

Referring to FIGS. 1, 2 and 4, a central window 64 and indentations or tabs 66 are formed in the top surface 54 of the lid 14 and are generally aligned with the center aperture 34 of the tray 12. When a cartridge 22 is seated within the center aperture 34 of the tray 12, the central window 64 and tabs 66 allow portions of the cartridge 22 to be exposed, with the remaining portions of the cartridge 22 covered and secured by the lid 14. As such, the lid 14 functions to secure the cartridge 22 within the packaging system 10 during storage and/or use of the system/device 10.

As with the tray 12, the lid 14 of the packaging system 10 also includes one or more longitudinal side-slots 68. The side-slots 68 are positioned on either side of the indentations/tabs 66 and are designed to accommodate the guideposts of the cover 16. To further understand the interaction between the side-slots 68, 40 of the lid 14 and tray 12 and the guideposts of the cover 16, it is instructive to first describe the cover 16, making reference to FIGS. 1, 2, 5, 6 and 7.

Figure 5:
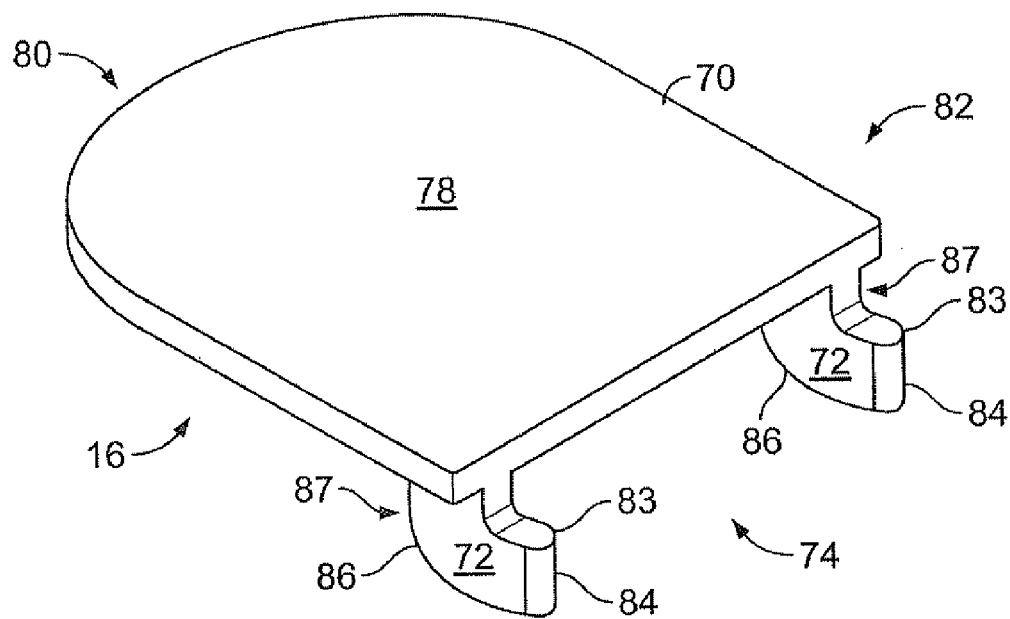
FIG. 5 is a perspective view of an embodiment of a cover of a lens packaging system in accordance with the present invention.
Figure 6:
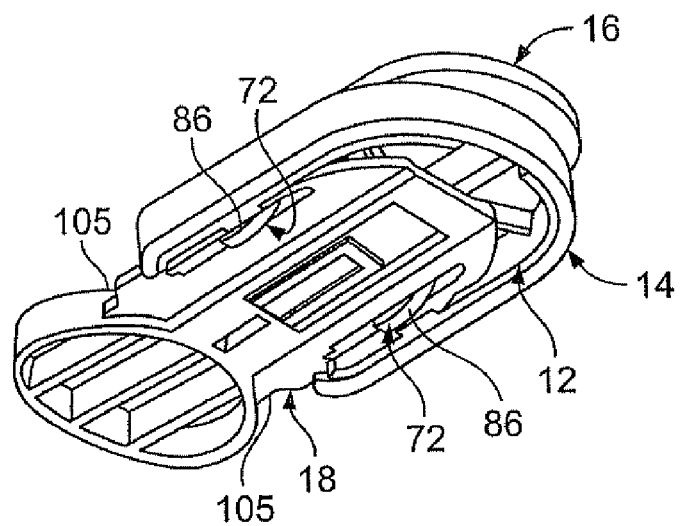
FIG. 6 is a perspective view of the underside of an embodiment of a lens packaging system in accordance with the present invention.
Figure 7:
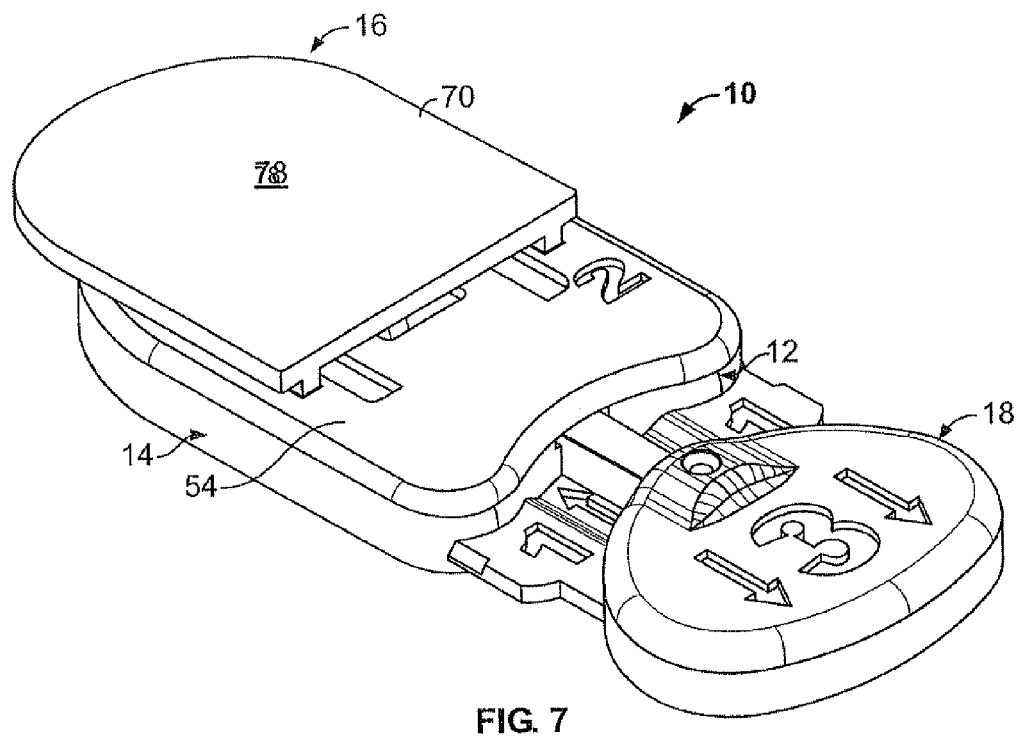
FIG. 7 is an alternate perspective view of the lens packaging system of FIG. 6.

FIG. 5 depicts an embodiment of the cover 16 as used in the packaging system 10. The cover 16 preferably includes a generally planar or flat body 70 and two guideposts 72. The body 70 of the cover 16 further includes a top surface 78 and a bottom surface (not visible) that are shaped similar to the top surfaces 28, 54 of the tray 12 and lid 14. The body 70 is preferably configured in a half-oval shape that includes a rounded or curved distal end 80 and a relatively straight or linear proximal end 82. As seen in FIGS. 6 and 7, the body 70 of the cover 16 is sized to cover a substantial portion of the top surface 54 of the lid 14 and, in particular, at least a portion of the central window and indentations of the lid 14.

The guideposts or guide elements 72 of the cover 16 may also be relatively planar or flat, but lie in vertical planes that are perpendicular to the plane of the cover's bottom surface. Each guidepost 72 is configured approximately in the shape of a quarter-circle and includes a first or longitudinal straight edge 83, a second or vertical straight edge 84 and a rounded edge 86. The first straight edge 83 of each guidepost 72 extends parallel to the bottom surface of the cover 16, while the second edge 84 is preferably positioned at approximately a ninety-degree angle from the first straight edge near the proximal end 82. A notch 85 is formed in the portion of the guidepost 72 where the first and second edges 84 intersect, the area around the notch 85 forming a type of neck or stem region 87. The stem region 87 is configured to seat within the narrow portion of the L-shaped slot 40 of the tray 12, as explained in further detail below. The remaining rounded edge 86 of the guidepost 72 connects the first and second edges 84 of the guidepost 72, thereby forming its generally quarter-circle shape. As referenced above, each guidepost 72 is sized to fit within the longitudinal side-slots 40, 68 of the tray 12 and lid 14. The guideposts 72 are generally parallel to each other and symmetrically positioned near the side edges of the cover 16, which generally correspond to the side edges of the lid 12 and tray 14.

As noted in the Background of the Invention as set forth above, there is a need for a packaging system 10 that enables a user to easily transfer an IOL 20 into a cartridge 22 without damaging the IOL 20 or compromising its sterility. As the lens packaging system 10 substantially eliminates these undesirable characteristics, it is instructive to particularly describe the loading tool 18 that reliably drives or transfers the IOL 20 into the cartridge 22 while maintaining IOL sterility. For this purpose, reference is made to FIGS. 1, 2 and 8.

Figure 8:
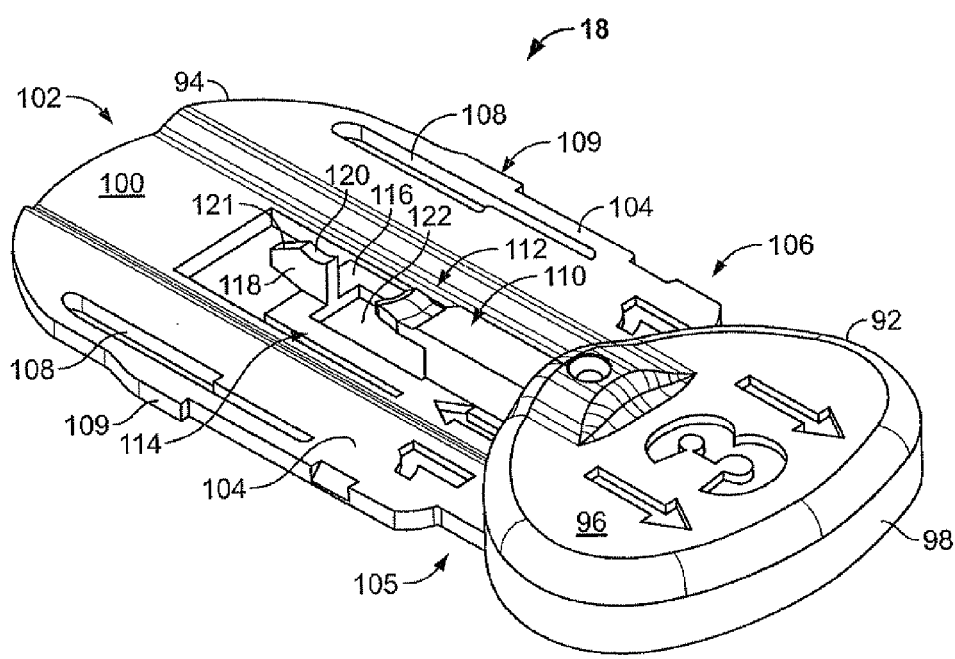
FIG. 8 is a perspective view of an embodiment of a loading tool of a lens packaging system in accordance with the present invention.

FIGS. 1, 2 and 8 illustrate one embodiment of the loading tool 18, which includes a oval-shaped handle 92 in communication with a half-oval shaped slide 94. In general, the handle 92 of the loading tool 18 includes a circular pushing surface 96 and a sidewall 98 that extends around the perimeter of the surface 96. The sidewall 98 provides additional structural support and gives added dimension to the handle 92 to enable a user to securely and controllably grip the loading tool 18 of the system. As seen in FIGS. 2 and 8, the half-oval shaped slide 94 is connected to the handle 92 of the loading tool 18 via the sidewall 98.

As with the cover 16, the slide 94 of the loading tool 18 includes a generally planar or flat body 100 having a top surface and a bottom surface that are shaped similar to the top surfaces 28, 54 of the tray 12 and lid 14. In this regard, the slide 94 of the loading tool 18 is configured in a half-oval shape that includes a generally rounded or curved distal end 102, two side-edges 104 and a proximal end 106 that follows the outline-shape of a portion of the sidewall 98. Overall, the slide 94 is sized to fit through the opening 46 of the sidewall 44 and within the tray 12 of the packaging system 10.

As seen in FIGS. 2, 6 and 8, one or more indentations 105 are located along the side-edges 104 and near the proximal end of the planar body 100 of the loading tool 18. These indentations 105 are configured to bypass the portion or section of the lid's sidewall 52 that surrounds or frames the lid's notches 62. In particular, during storage, the indentations 105 of the loading tool 18 are positioned proximal to and outside of the notches 62 of the lid 14. As such, the wider, non-indented section of the loading tool 18 is seated within the notches 62 during storage so that the lid 14 cannot be removed from the system or device 10. However, when the loading tool 18 is actuated or advanced distally, the indentations 105 fall into alignment with the notches 62, thereby allowing lid removal.

Referring to FIGS. 2 and 8, each side-edge 104 of the slide 94 further includes one or more detents 109 which are configured to interact with the detent-slots 111 of the tray 12. Adjacent the detents 109 is a groove or slot 108 that extends along a longitudinal length of the slide 94. The grooves 108 are configured to accommodate the guideposts 72 of the cover 16 when the loading tool 18 is in a fully retracted or non-actuated position, as shown in FIG. 6, for example. In addition, the grooves 108 also allow sufficient inward movement of the side-edges of the loading tool 18 to enable the detents 109 to pop out of the detent-slots 111 of tray 12 and travel along the inside sidewall of the tray 12 during device activation.

In this regard, prior to device activation, the detents 109 of the loading tool 18 are seated within the detent-slots 111 of the tray 12. To prevent unintentional device activation by dislodging the detents 109 from the detent-slots 111 via distal sliding movement of the loading tool 18, the guideposts 72 of the cover 16 are seated within the slots 68, 40, 108 of the lid 14, tray 12 and loading tool 18 and, in particular, are aligned with the detents 109 and detent-slots 111. As such, the guideposts 72 prevent the detents 109 from causing the side-edges of the loading tool 18 to bow inward along the grooves 108 and from becoming dislodged from the detent-slots 111 of the tray 12. Thus, the guideposts 72 of the cover 16 serve, in part, to secure the system 10 during shipping and storage by preventing lateral distal advancement of the loading tool 18.

Proximal to the grooves 108 and located near the central, longitudinal axis of the slide 94 is a IOL support member 110. Referring to FIGS. 8-11, the distal end 112 of the support member 110 includes a beveled and/or curved front edge formed to securely contact a portion of the IOL's perimeter and aid in advancing the IOL 20 into the cartridge 22. The distal end 112 further includes a groove located in the top surface of the support member 110 to securely hold a first or trailing haptic 113a of the IOL 20.

Figure 9:
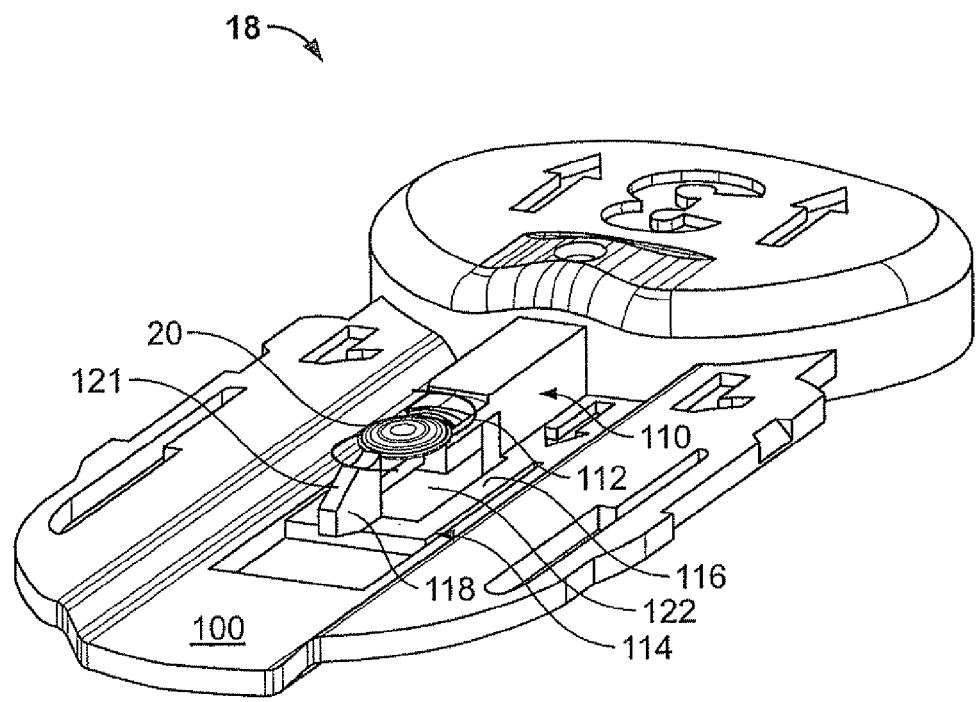
FIG. 9 is a perspective view of an IOL loaded within a loading tool in accordance with the present invention.
Figure 10:
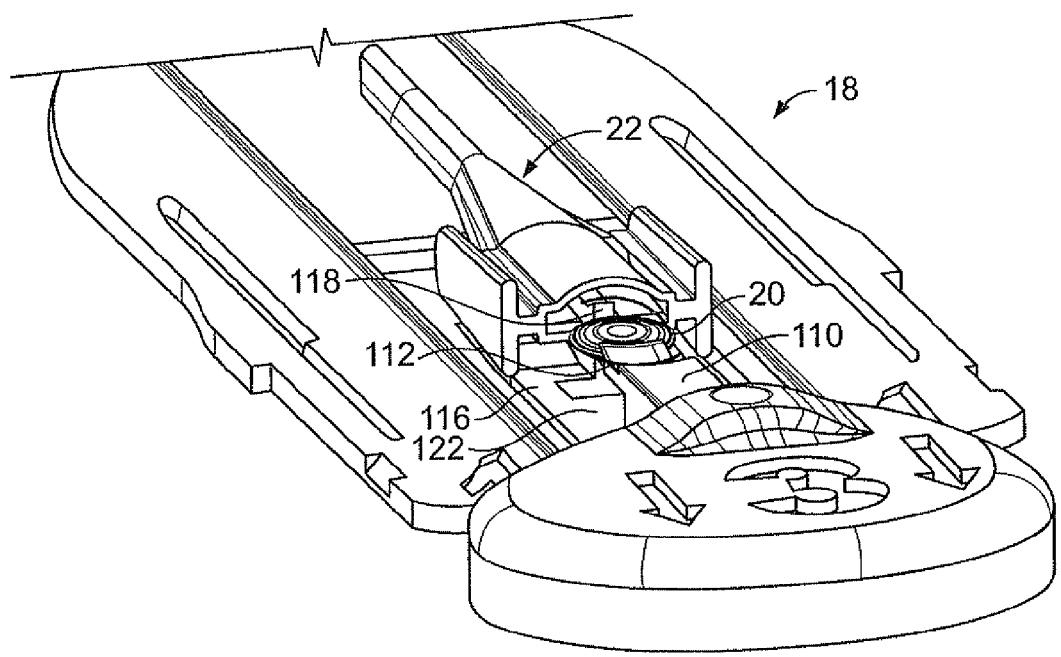
FIG. 10 is a perspective view of an IOL and cartridge loaded within a loading tool in accordance with the present invention.
Figure 11:
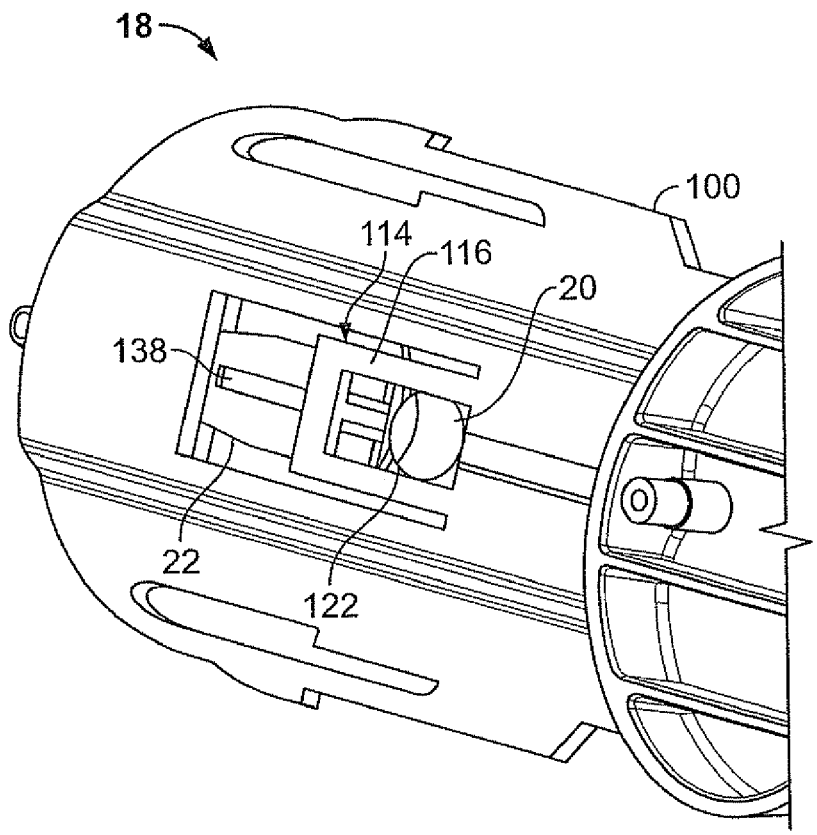
FIG. 11 is an alternate perspective view of the underside of the lens packaging system of FIG. 10.

Distal to the support member 110 is a guide member 114. As seen in FIGS. 8, 9, and 11, the guide member 114 includes a semi-flexible, U-shaped base 116 and a wedge-shaped holder 118. The forked end of the U-shaped base 116 extends longitudinally toward the proximal end 106 and is integrally formed with the body 100 of the push-rod 18. Located along the distal end and perpendicular to the planar, U-shaped member 116 is the wedge-shaped holder 118. The wedge-shaped holder 118 includes a notched or grooved top surface 120 and a sloping front end 121. Similar to the support member 110, the grooved top surface 120 of the guide member 114 is configured to securely hold the second or leading haptic 113b of the IOL. As such, during the delivery or transfer procedure (explained in further detail below), the support member 110 and guide member 114 not only aid in advancing the IOL 20 into the cartridge 22, but also in controlling the IOL's rotational movement so that the IOL 20, and in particular the leading haptic 113b of the IOL 20, is correctly positioned within the cartridge 22.

Referring to FIGS. 9 and 11, the U-shaped base 116 of the guide member 114 forms a central through-hole or window 122 in the body 100 of the loading tool 18. The window 122 enables a user of the device 10 to access a portion of the IOL 20 prior to IOL transfer into the cartridge 22. As such, when the IOL 20 is seated on the loading tool 18 and in direct alignment with the loading tool's window 122, a user of the packaging system 10 may easily apply a lubricant, viscoelastic gel or viscoelastic surgical device (VSD) (not shown) to the IOL 20.

In general, a VSD is injected into the eye to help maintain the shape of ocular structures and as a lubricant/coating to minimize trauma from surgical instruments and implants. In addition, viscoelastic may also be used with IOLs as a form of lubricant to aid in the passing of the IOL 20 into and through the cartridge 22 and to help prevent air bubbles from being delivered into the eye with the IOL 20, which would obstruct the surgeon's view during the IOL insertion procedure.

Figure 12:
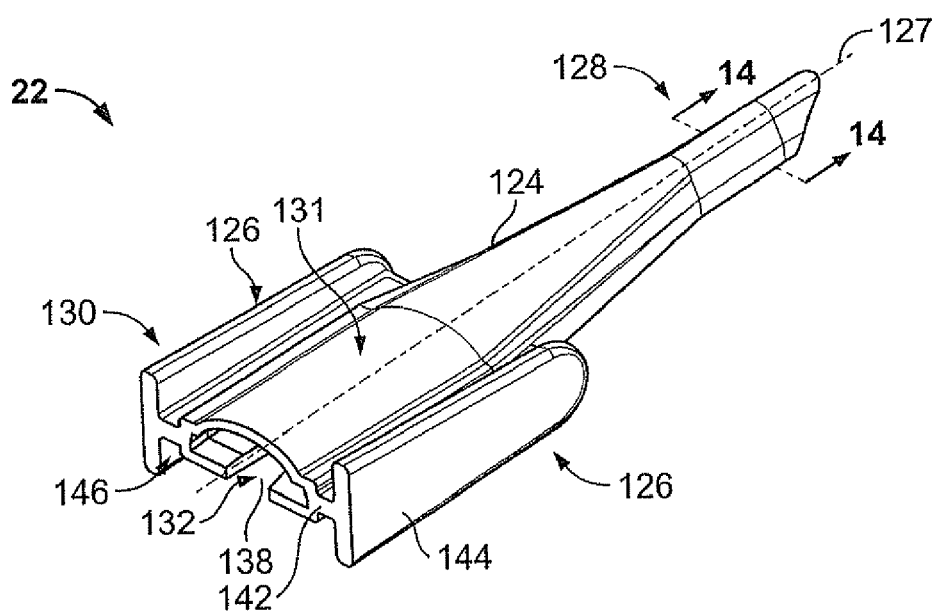
FIGS. 12 and 13 illustrate perspective views of an embodiment of a cartridge in accordance with the present invention.
Figure 13:
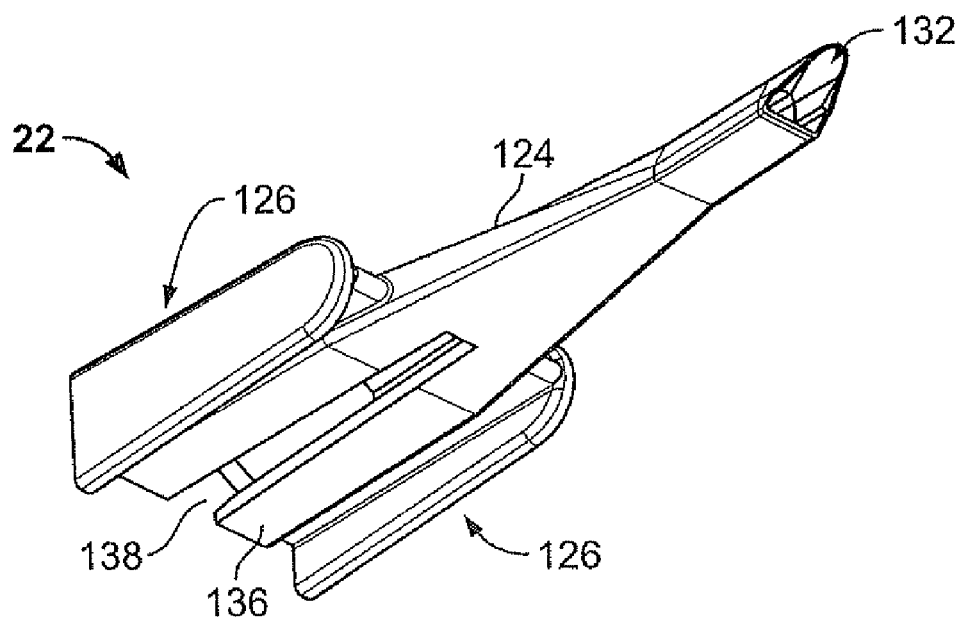

FIGS. 12 and 13 illustrate one preferred embodiment of the cartridge 22 for delivering an intraocular lens into the eye of a subject. The cartridge 22 includes an elongate tubular body 124 and two wings 126 longitudinally disposed to either side of the body 124 and formed along a proximal portion of the exterior sides of the body 124. The elongate body 124 is disposed along a longitudinal axis 127 and includes a distal end 128, a proximal end 130 and a tapering, longitudinal lumen 132 that extends along the axial length of body 124. The lumen 132 comprises a load chamber 131 disposed at the proximal end 130 of the body 124 for receiving or loading the IOL 20 and an aperture 133 disposed at the distal end 128 of the body 124 for delivering the IOL 20 into the eye of a subject. The lumen 132 or inside profile of the cartridge 22 is generally symmetrical about the longitudinal axis of the cartridge 22 and sized to accommodate the rod tip of the handpiece (not shown) during the insertion procedure.

Figure 14:
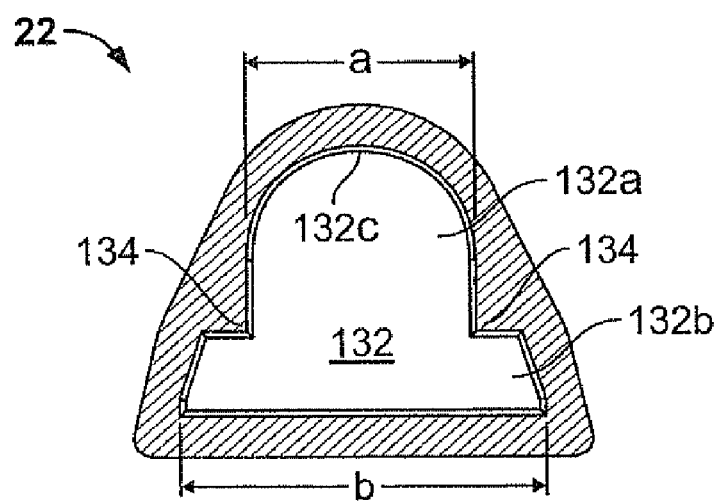
FIG. 14 illustrates a sectional view distal to the wings of the cartridge in accordance with the present invention.
Figure 25:
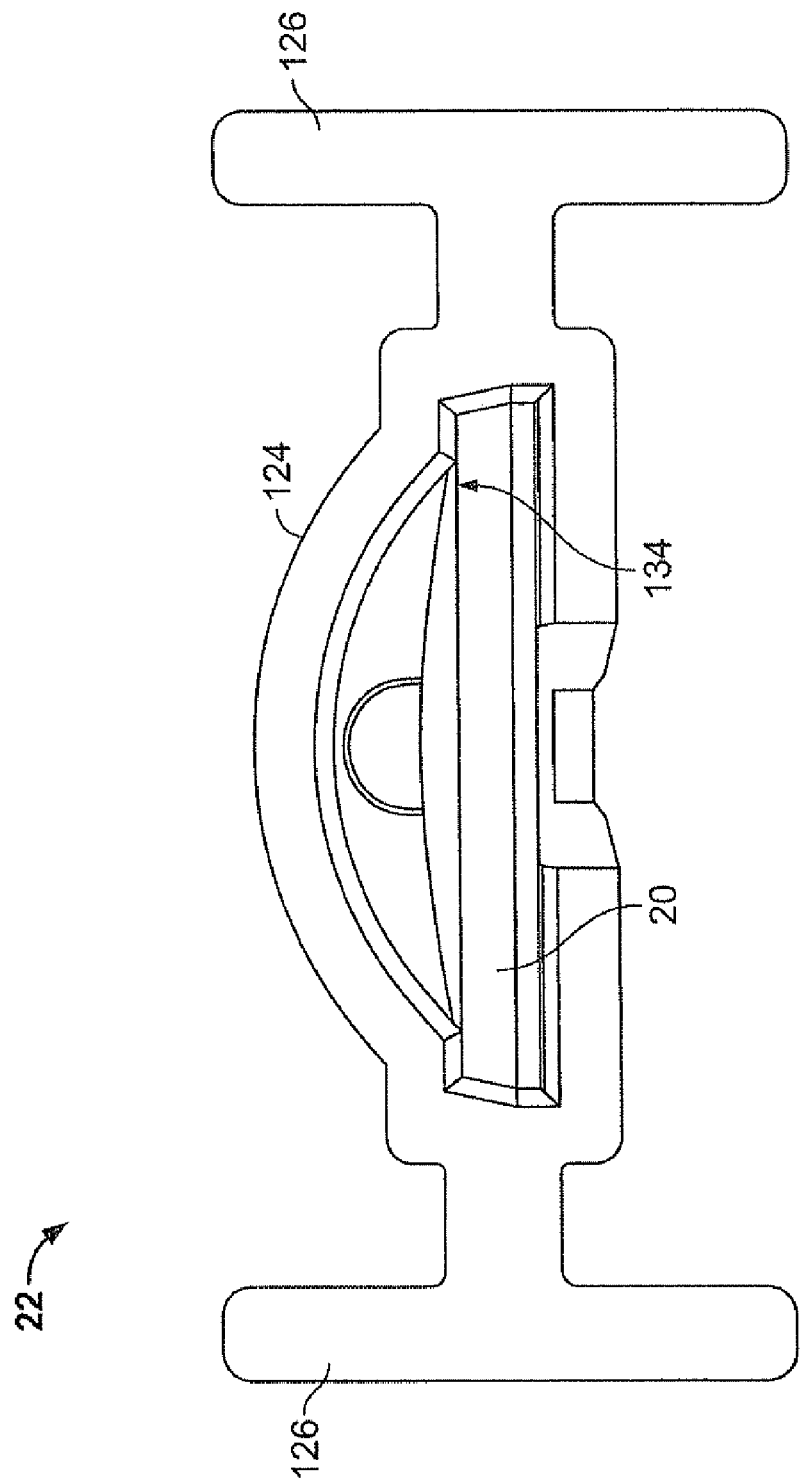
FIG. 25 illustrates an embodiment of a cartridge with an IOL positioned therein in accordance with the present invention.
Figure 26:
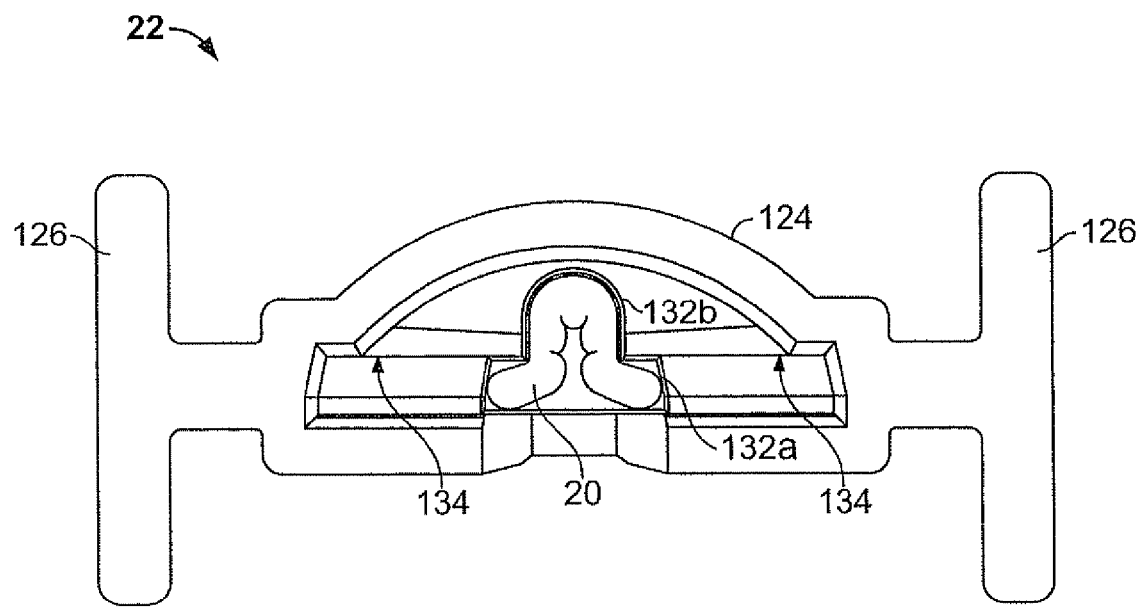
FIG. 26 illustrates an embodiment of a cartridge with an IOL advanced toward the distal end of the cartridge in accordance with the present invention.

Referring to FIG. 14, the aperture 133 and the cross-sectional shape of the lumen 132 near the aperture 133 generally comprises an upper portion 132a and a lower portion 132b. The upper portion 132a in cross-section is generally arcuate or dome shaped and has a width a, while the lower portion in cross-section is generally horizontally disposed and has a width b that is preferably greater than the width a. The bottom of lower portion 132b is preferably generally flat, as illustrated in FIG. 14, but may alternatively be arcuate in shape, for instance to increase or decrease the cross-sectional area of the lumen 132 at or near the aperture 133. When the lumen 132 is used to deliver the IOL 20, as illustrated in FIGS. 25 and 26, the center of the IOL 20 is generally disposed in the upper portion 132a, while portions of the edges of the IOL 20 are substantially disposed in the lower portion 132b.

The interior surface of the lumen 132 also includes one or more ribs 134 that extend substantially along the longitudinal length of the body 124. The triangular-shaped ribs 134 may extend from the loading area or proximal end 130 to the discharge area or distal end 128 of the cartridge 22. The ribs 134 function, at least in part, to fold or compress the edges of the IOL in a controlled manner toward the outer edges of the interior of the cartridge 22.

In one embodiment of the cartridge 22, the symmetry of the body 124 allows for even or uniform application of a coating to the interior surface simply using a spray apparatus. The cross-sectional area of the distal end of the lumen 132 is generally smaller than or reduced relative to the cross-sectional area of the proximal end of the lumen 132, as a result of the cartridge's tapered lumen 132. The taper of the lumen 132 aids in compressing or folding the IOL 20 as the IOL 20 passes through the lumen 132 of the cartridge 32 and into the patient's eye, as described in further detail below.

In addition to providing guiding means for the IOL 20, the interior surface or inside edges of the cartridge 22 also may be configured to accommodate the shape of the IOL 20. This feature not only provides additional control during IOL transfer into the cartridge 22, but allows more efficient use of space to compress and guide the IOL 20 to the distal end 128 of the cartridge 22. For example, in one embodiment of the invention (not shown), the inside edges of the cartridge 22 are configured to mimic the shape of the AMO OptiEdge® IOL. The reduced friction between the IOL 20 and the interior wall of the cartridge 22 results in less force being needed to deform or compress the IOL 20 as it is pushed/advanced to the distal end 128 of the cartridge 22.

Referring back to FIGS. 10-13, a portion of the bottom surface 136 of the cartridge 22 includes an opening 138 which allows the wedge-shaped holder 118 of the loading tool 18 to extend therethrough and support the leading haptic 113b of the lens 20 during shipping and storage of the device 10 and loading of the IOL 20 into the cartridge 22. In this regard, the opening 138 provides a means of guiding the leading haptic 113b in a forward direction toward the distal tip of the cartridge 22 when the IOL 20 is advanced into the cartridge 22. The opening 138 of the cartridge 22 may also be configured to allow a portion of the rod-tip of a handpiece to contact and/or push the IOL 20 through and out of the cartridge 22 during the insertion procedure. The opening 138 is preferably in the form of an elongated slot that is open at the proximal end 130 of the body 124, as illustrated in FIG. 13. Alternatively, the opening 138 may have other shapes, lengths, or aspect ratios depending upon the particular design requirements of the IOL 20, the cartridge 22, the loading tool 18, or the inserter and pushrod used to deliver the IOL 20 into the eye of a subject.

Figure 15:
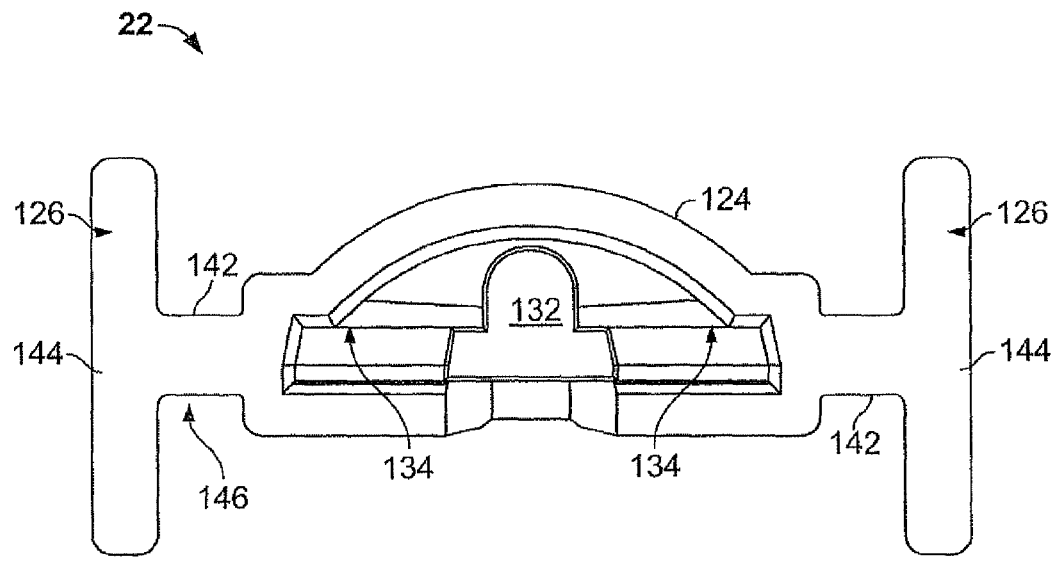
FIG. 15 illustrates a proximal end view of the loading end of a cartridge in accordance with the present invention.

As shown in FIG. 15, each of the wings 126 formed along the exterior side near the proximal end of the cartridge 22 include a rectangular-shaped connecting rib 142 and finger grip 144. In one embodiment, the connecting rib 142 extends along the longitudinal length of the proximal end 130 of the cartridge 22 and connects the finger grip 144 to the body 124 of the cartridge 22. Perpendicular to the connecting rib 142 is the rectangular-shaped finger grip 144. Although the finger grip 144 is illustrated as being rectangular in shape, it is understood that the finger grip 144 of the cartridge 22 can be configured in various shapes, sizes and textures, which allow a user of the device 10 to securely grasp the cartridge 22. The finger grip 144, connecting rib 142 and a portion of the cartridge body 124 form an exterior slot or groove 146 that is configured to mate with and snap into the distal end of a handpiece.

Figure 16:
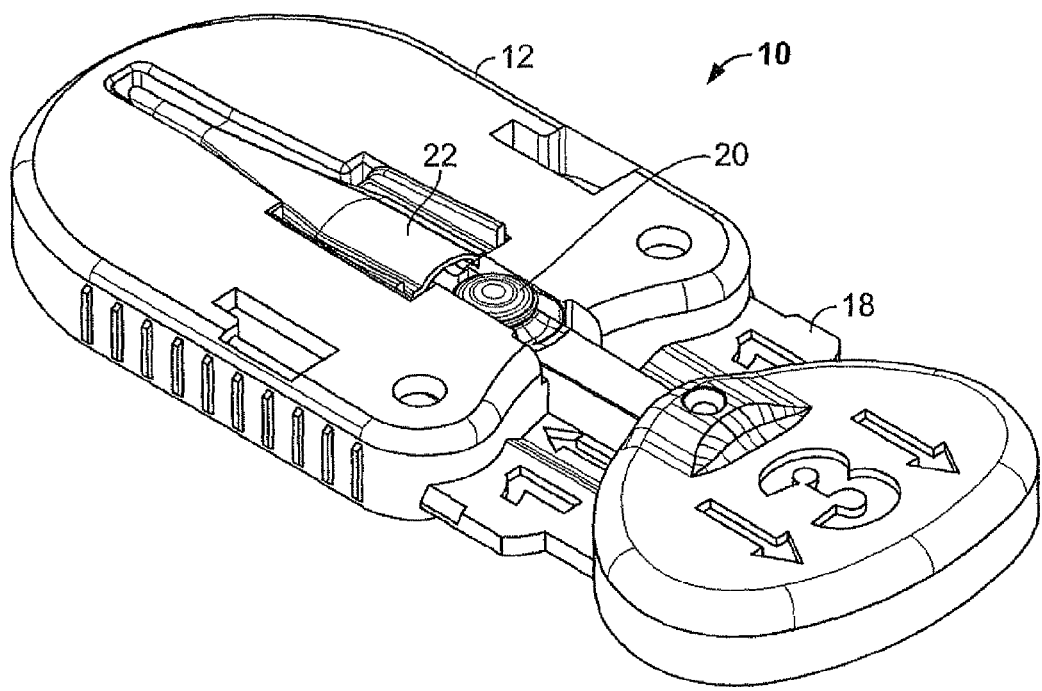
FIG. 16 illustrates an alternate embodiment of a lens packaging system with a lens and cartridge preloaded therein and the cover and lid removed in accordance with the present invention.

Referring to FIG. 16, in certain embodiments, the loading tool 18 and the cartridge 22 are mounted into the tray 12. The IOL 20 is preferably placed onto the IOL support member 110 of the loading tool 18 and disposed for loading into the load chamber 131. Prior to shipment or storage, the lid 14 and the cover 16 are preferably placed over the tray 12 in order to protect the IOL 20 and prevent premature loading of the IOL 20 into the load chamber 131.

To minimize and/or eliminate damage to the IOL during loading into the cartridge 22, a viscoelastic or other substance may be applied to both the IOL 20 and cartridge 22 of the device 10. As previously discussed, the window 122 in the loading tool 18 enables a user to apply viscoelastic to the IOL 20. Similarly, the opening 138 in the cartridge 22 also enables a user of the device 10 to easily administer viscoelastic into the cartridge 22. As such, the viscoelastic lubricates the surfaces of the cartridge 22 and IOL 20, thereby mitigating any tearing of the IOL 20 as it travels through the cartridge 22 and reducing the incidence of tissue trauma to the eye.

Figure 17:
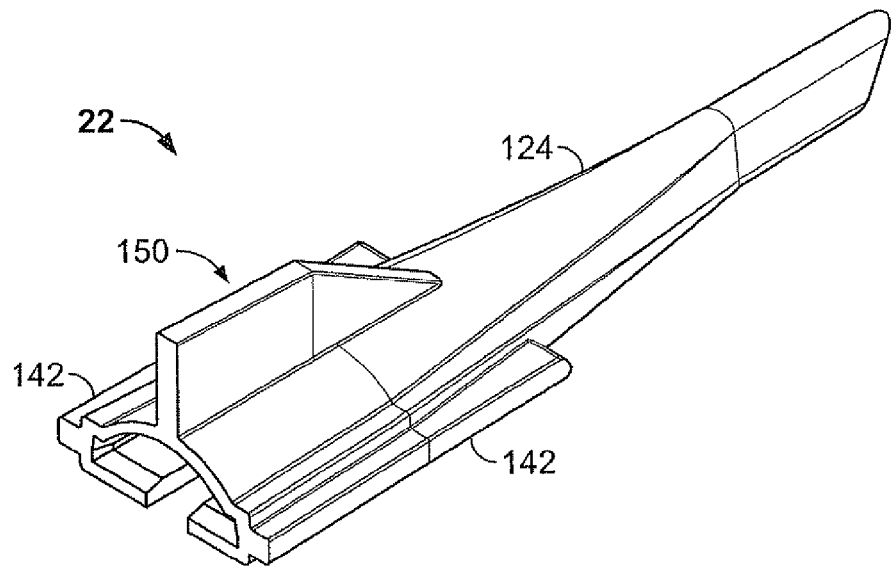
FIGS. 17-19 illustrate an alternate embodiment of a cartridge in accordance with the present invention.
Figure 18:
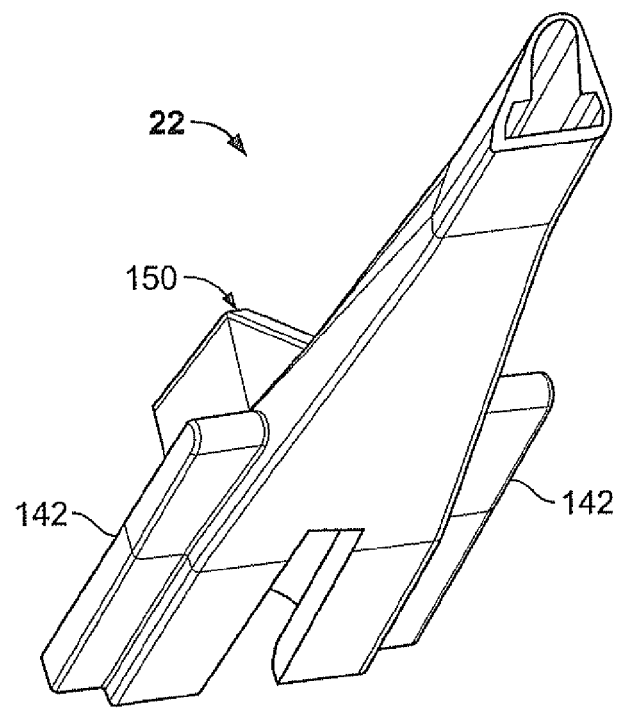
Figure 19:
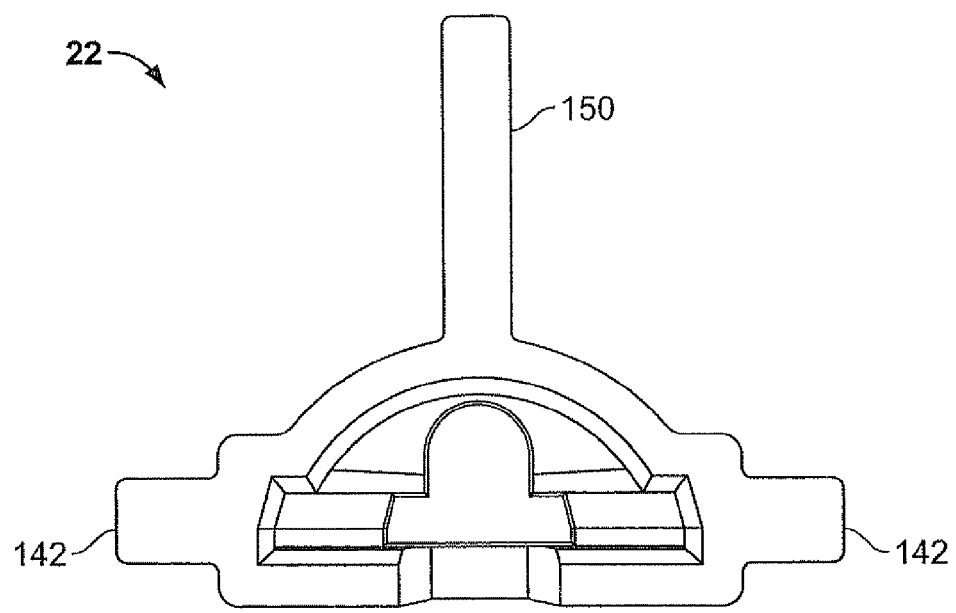
Figure 20:
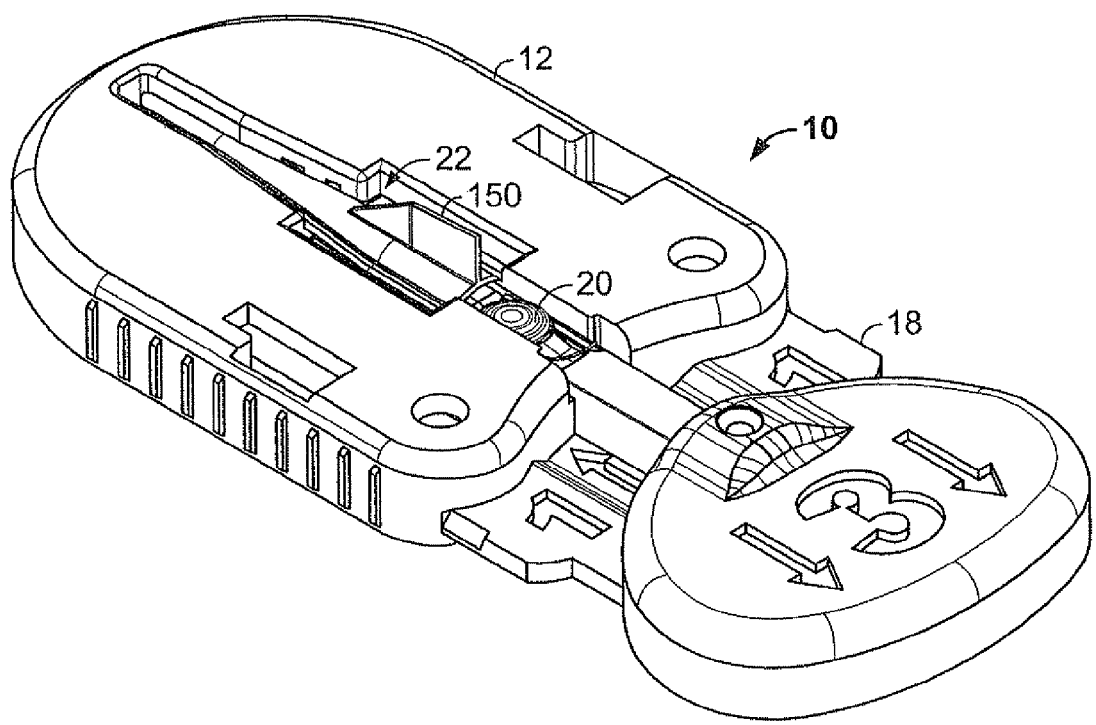
FIG. 20 illustrates an embodiment of a lens packaging system with a lens and cartridge preloaded therein and the cover and lid removed in accordance with the present invention.

Referring to FIGS. 17-19, an alternate embodiment of the cartridge 22 is illustrated in which the finger grips 144 of the wings 126 have been removed and a holding handle 150 has been added to top, exterior surface near the proximal end 130 of the cartridge 22. Referring to FIG. 20, the cartridge 22 illustrated in FIG. 17 is shown mounted in the tray 12 along with the loading tool 18 and the IOL 20.

In certain embodiments, the cartridge 22 is used in conjunction with a handpiece to deliver the IOL 20 into the eye of a subject. For example, FIGS. 21-24 illustrate a handpiece 140 which is configured to hold the cartridge 22, preferably after the loading tool 18 has been used to mount the IOL 20 into longitudinal lumen 132.

Figure 21:
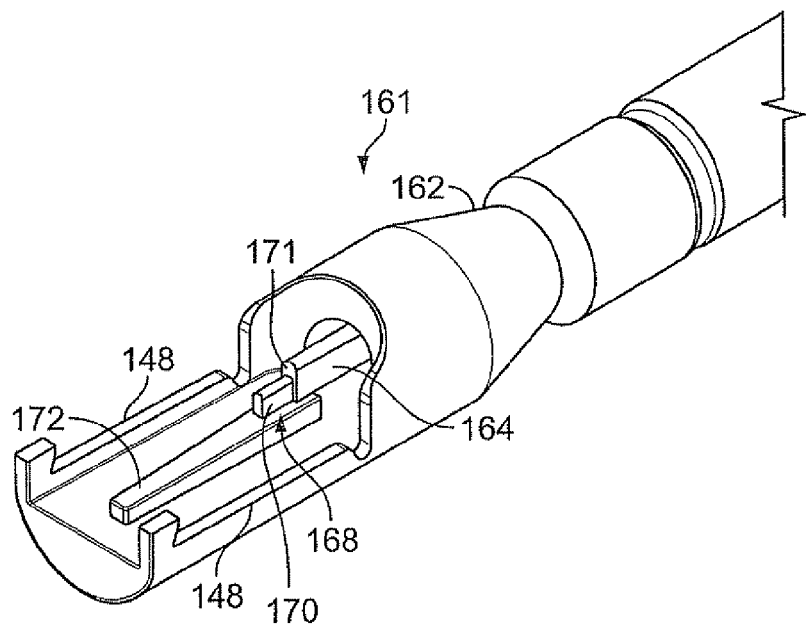
FIG. 21 illustrates an inserter in accordance with the present invention.
Figure 22:
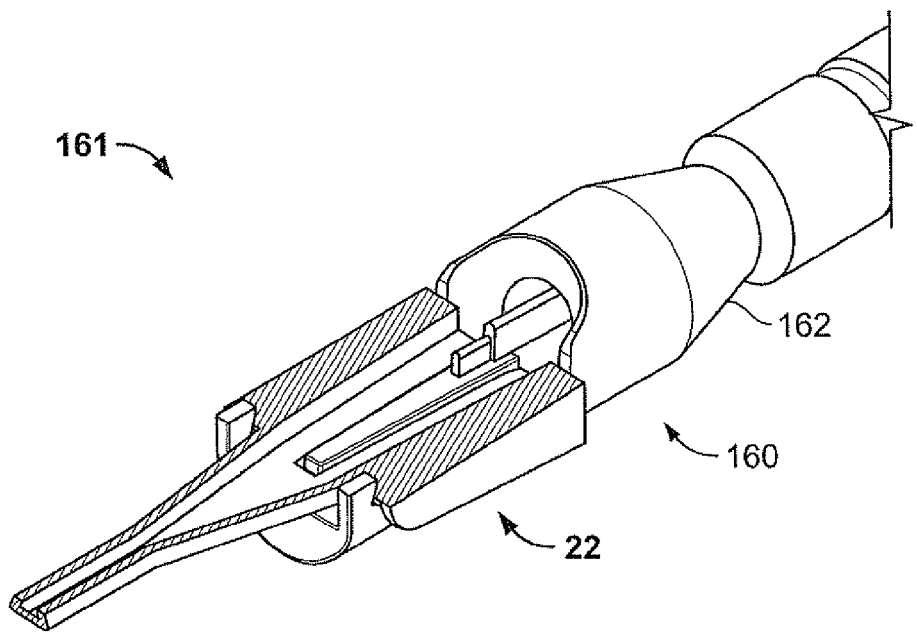
FIG. 22 illustrates an insertion system in accordance with the present invention.
Figure 23:
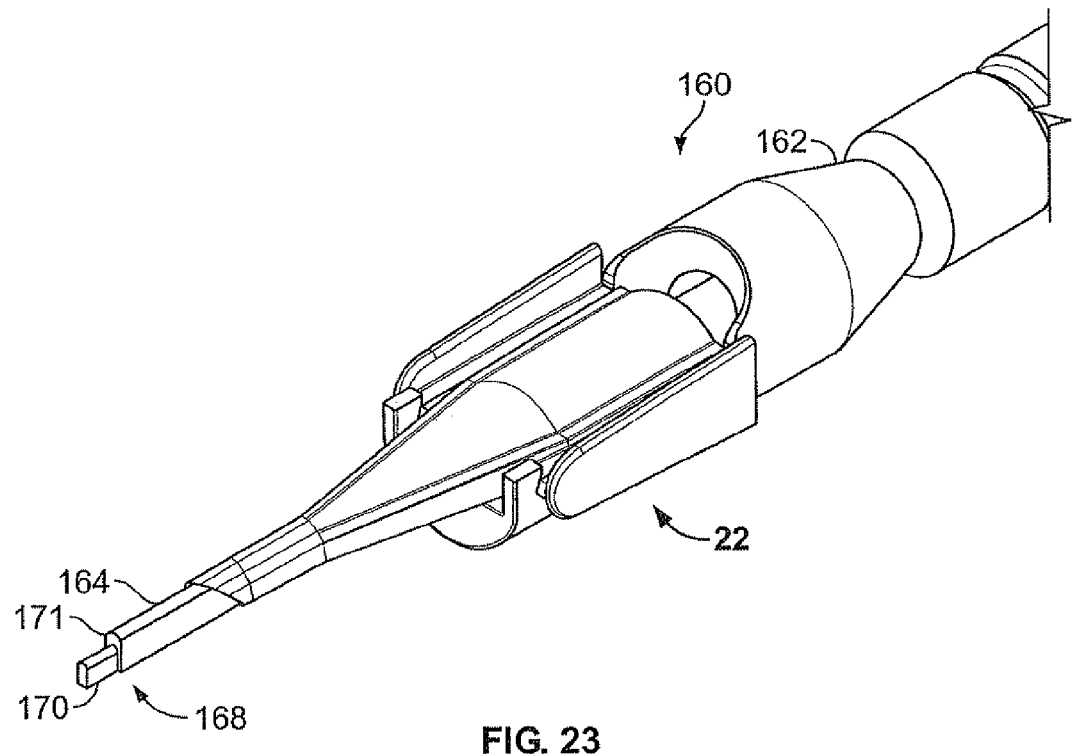
FIG. 23 illustrates the insertion system shown in FIG. 22 with a pushrod extending distally from a cartridge.

In certain embodiments, an insertion system 160 for delivering the intraocular lens 20 into the eye of a subject comprises the cartridge 22 and an inserter 161. The inserter 161 comprises a handpiece 162 and a pushrod 164 with a tip 168 having a saddle 170. The saddle 170 preferably has a smaller diameter than the remainder of the pushrod 164, such that a ledge 171 is formed between the saddle 170 and the remaining portions of the pushrod 164, as illustrated in FIGS. 21 and 23. The opening 138 on the bottom surface 136 of the cartridge 22 is disposed to permit passage of at least a portion of the tip 168 when cartridge is placed onto the handpiece 162 from above the handpiece 162. In certain embodiments, the handpiece 162 further comprises a raised platform 172 disposed below pushrod 164, the raised platform 172 being sized to fit within the opening 138. The platform 172 may be configured to fit tightly within the opening 138, for instance, to aid in securely maintaining the cartridge 22 when attached to the handpiece 162; however, a tight fit between the opening 138 and the platform 172 is not essential.

In certain embodiments, the insertion system 160 further comprises at least a portion of the lens packaging system/lens loading system 10 for storing the IOL 20 and/or for placing the IOL 20 in the cartridge 22. For instance, the system 160 may include the tray 12 and the loading tool 18. Additionally, the system 160 may include the lid 14 and the cover 16, for instance, in order to protect the IOL 20 and prevent premature loading of the IOL 20 into the load chamber 131. The IOL 20 is preferable place inside the packaging system 10 prior to storage and/or shipment to a customer or user. Alternatively, at least portions of the system 10, for example the tray 12 and the loading tool 18, may be stored or shipped as separate parts. A practitioner may then use the portions of the packaging system 10 to load the IOL 20 inside the load chamber 133 of the cartridge 22 just prior to placing the IOL inside an eye using the handpiece 162.

As seen in FIG. 21, the distal end of the handpiece 140 includes two rails or side-edges 148 having slightly curved proximal and distal ends. The rails 148 are sized and shaped to fit securely within the grooves 146 of the cartridge 22, with the distal ends of the rails 148 having a greater curved depth than the proximal ends. In this regard, when the cartridge 22 is inserted within the handpiece 140, the distal ends of the cartridge grooves 146 are first slid into the curved distal ends of the rails 148. Once the distal ends of the grooves 146 abut the distal ends of the rails 148, the proximal ends of the grooves 146 are then inserted downward and preferably snapped into the curved proximal ends of the rails 148. The snap-fit between the grooves 146 and the rails 148 keep the cartridge 22 securely within the handpiece 140 during the lens delivery procedure.

The packaging system 10 is typically supplied to an end-user or surgeon with a lens cartridge 22 and IOL 20 pre-loaded within the tray 12. FIGS. 16 and 20 illustrate embodiments of the packaging system as supplied to the end user with the cover 16 and lid 14 removed to clearly show the lens 20 and cartridge 22 within the device 10. Alternatively, the packaging system 10 may only include the IOL 20, thereby allowing the user of the device 10 to supply the cartridge 22.

Prior to use, the tray 12 of the device 10 is covered with the lid 14 and the loading tool 18 is a retracted or partially inserted position within the opening 46 of the tray 12. In addition, the cover 16 is secured to the lid 14, tray 12 and loading tool 18, via the guide elements 72 and slots 40, 68, 108, to prevent inadvertent or unintentional activation of the system 10. In particular, as described above, the guideposts or vertical members 72 of the cover 16 block further distal advancement of the loading tool 18, and its support member 110, until the cover 16 is removed from the system 10.

During use of the device/system 10, the cover 16 is removed to expose the top surface 54 of the lid 14. Preferably, the lid 14 is fabricated from a clear material to allow the user of the device 10 to inspect the system 10, particularly the lens cartridge 22 and IOL 20, prior to use to ensure that none of the components are damaged. Removal of the cover 16 also exposes the central window 64 of the lid 14 and, thereby, a portion of the lens cartridge 22. Viscoelastic fluid is applied to the cartridge 22 and/or the IOL 22 through the opening 138 and window 122, respectively, prior to device activation.

To activate the device 10, a user may simply grasp the handle 92 of the loading tool 18 using, for example, his/her thumb and fore-finger, and push the loading tool 18 in a distal direction. Longitudinal sliding movement of the loading tool 18 causes the distal tip 112 of the support member 110 to push the IOL 20 along the longitudinal slot of the tray 12 and into the lumen 132 of the cartridge 22.

Further advancement of the loading tool 18 causes the U-shaped base 116 of the guide member 114 to advance along the outside surface of the cartridge body 124, whereas the wedge-shaped holder 118 travels through the opening 138 of the cartridge 22. Full or complete advancement of the loading tool 18 causes the holder 118 and support member 110 to deposit the IOL 20 within the cartridge 22.

After the loading tool 18 is fully advanced and the IOL 20 is properly positioned within the cartridge 22, the lid 14 of the packaging system 10 is then removed. Next, the loading tool 18 is proximally retracted to release the loaded cartridge 22 from the loading tool 18 and the loaded cartridge 22 is then removed from the packaging system. At this point, the user may easily transfer the cartridge 22 with its loaded IOL 20 to the inserter 161 for delivery of the IOL 20 into a patient's eye.

In view of the above, the packaging system 10 may be used to simplify the removal and transfer of the IOL 20 to the IOL insertion system 160. In particular, the packaging device 10 enables a user to easily load an IOL 20 into a cartridge 22 without requiring the use of forceps. The configuration of the cartridge 22 also allows a user to fold and/or compress the IOL 20 during IOL delivery into the eye without damaging the IOt 20 and/or compromising IOL sterility. In addition, the related methods of operation minimize and/or eliminate the potential of damaging the IOL 20 during unpackaging, folding, transfer and/or loading procedures. Further, the device 10 and its method of use provide repeatable and consistent loading (e.g., with respect to position and rotation) of the IOL 20 into the cartridge 22.

Figure 24:
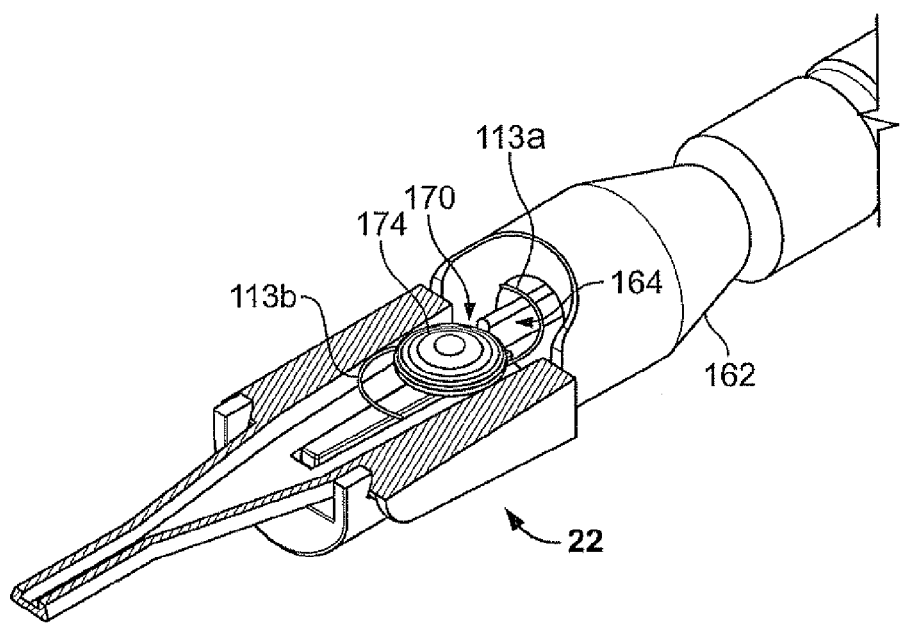
FIG. 24 illustrates the insertion system shown in FIG. 22 with an IOL draped over a saddle at the tip of a pushrod.

Referring to FIGS. 24-27, in certain embodiments, a method of inserting the IOL 20 comprises providing the cartridge 22 and providing the handpiece 140 with the pushrod 164 having the saddle 170 in the tip 168. The method further comprises disposing the cartridge 22 above the handpiece 140 and attaching the cartridge 22 onto the handpiece 140 from above the handpiece 140. While attaching the cartridge 22, the method also includes disposing the tip 168 such that the opening 138 permits passage of at least a portion of the tip 168, for instance, as illustrated in FIGS. 21 and 24.

Figure 27:
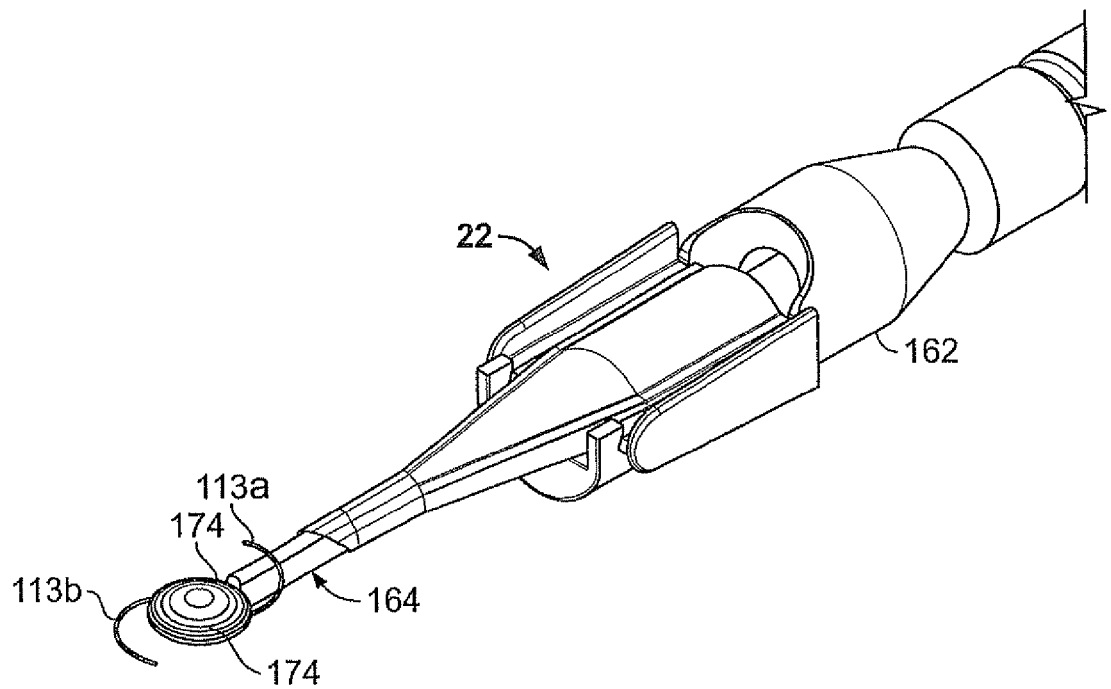
FIG. 27 illustrates the insertion system shown in FIG. 22 with an IOL extending distally from the cartridge.

The method may further comprises loading the IOL 20 in the cartridge 22, for instance by using the loading tool 18, as discussed above herein. The IOL 20 is preferably placed in the cartridge 22 prior to attaching the cartridge 22 onto the handpiece 162. Preferably, the IOL 20 is loaded into the load chamber such that at least a portion of at least one of the haptics 113a, 113b is disposed above at least a portion of the pushrod, as illustrated in FIG. 24. It is also preferable that the IOL 20 is loaded into the load chamber 22 such at least a portion of an optic body 174 of the IOL 20 is disposed above or draped over the saddle 170 of the tip 168, for instance, as illustrated in FIGS. 24 and 27.

Preferably, the method comprises advancing the IOL 20 along the lumen 132 and into the eye of a subject at least in part by engaging an edge of the optic body 174 of the IOL 20 with the ledge 171 at the tip 168 of the pushrod 164. By engaging the edge of the optic body in this manner, the ledge 171 may be used to help prevent the pushrod 164 from moving too far into the optic body 174, thereby advantageously preventing the pushrod 164 from damaging the optic body 174. The ledge 171 may also be used to more evenly distribute the force produced by the pushrod 164 around the edge of the optic body 174.

Initially, the IOL 20 is disposed in the load chamber 131 in a substantially flat and substantially unstressed state, as illustrated FIGS. 24 and 25. As the IOL 20 advances down the lumen 132, the optic body 174 of the IOL 20 is folded or squeezed such that the central portions of the IOL 20 fill the upper portion 132b of the lumen 132, as illustrated in FIG. 26. By contrast, the edges of the optic body 174 of the IOL 20 largely are contained within the lower portion 132a of the lumen, thereby advantageously allowing the orientation of the IOL 20 to be maintained as it advances down the lumen 132 and into the eye of the subject. In certain embodiments, as illustrated in FIG. 27, this allows the IOL 20 to exit the aperture 133 of the lumen 132 in substantially the same orientation as it had when it was in the load chamber 131.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention.

What is claimed is:

1. A cartridge for delivering an intraocular lens into an eye of a subject, comprising:
    a body disposed along a longitudinal axis having a distal end and a proximal end; and
    a tapered lumen disposed along the longitudinal axis having an aperture at the distal end of the body;
        the aperture and at least a portion of the tapered lumen each having a cross-section defined by two generally opposing and interfacing sides: a first side and a second side, wherein the interface of the two sides define a horizontal axis;
        the first side having a first width along the horizontal axis and a cross-section that is generally arcuate;
        the second side having a surface having a substantially flat portion that is generally parallel to the horizontal axis and that is wider than the first width.

2. The cartridge of claim 1, further comprising wings longitudinally disposed to either side of the body.

3. The cartridge of claim 1, wherein the body further comprises a bottom surface having an opening disposed along the longitudinal axis.

4. The cartridge of claim 3, wherein the opening comprises an elongated slot that is open at the proximal end of the body.

5. The cartridge of claim 3, wherein the opening is disposed to receive a tip of a pushrod of an inserter handpiece.

* * * * *